United States Patent [19]
Fleischmann

[11] 3,977,391
[45] Aug. 31, 1976

[54] PRESSURE SENSOR APPARATUS

[75] Inventor: Lewis Fleischmann, Randallstown, Md.

[73] Assignee: Hittman Corporation, Columbia, Md.

[22] Filed: July 16, 1974

[21] Appl. No.: 488,971

[52] U.S. Cl. .................. 128/2 A; 73/393; 73/410; 73/411; 128/2.05 D; 128/2.05 E; 250/336
[51] Int. Cl.² ......................... A61B 5/00
[58] Field of Search .......... 128/2 A, 2.05 D, 2.05 E, 128/350 R, 350 V, 1 R; 73/406, 407, 409–412, 418, 393; 250/336 R

[56] References Cited
UNITED STATES PATENTS

| | | | |
|---|---|---|---|
| 3,034,356 | 5/1962 | Bieganski et al. | 128/2.05 E |
| 3,503,402 | 3/1970 | Schulte | 128/350 V |
| 3,625,199 | 12/1971 | Summers | 128/2.05 E |
| 3,637,034 | 1/1972 | Wickenberg | 73/411 X |
| 3,686,958 | 8/1972 | Porter et al. | 73/406 |
| 3,715,927 | 2/1973 | Grant | 73/411 X |
| 3,789,667 | 2/1974 | Porter et al. | 73/406 |

*Primary Examiner*—Kyle L. Howell
*Attorney, Agent, or Firm*—Fleit & Jacobson

[57] ABSTRACT

A pressure sensor apparatus primarily for sensing pressure in a body cavity such as the cranium, bladder or vena cava of an animal or human comprising a Bourdon or bellows type pressure gauge connected to a flexible member such as a metallic disc or corrugated bellows tambour containing a non-radioactive fluid. A discrete mass of radioactive material is connected to the pressure gauge and moves proportionally to the pressure sensed by the flexible member. A radiation detector senses the movement of the radioactive material through a window in a radiation shield.

15 Claims, 6 Drawing Figures

PRESSURE SENSOR APPARATUS

CROSS-REFERENCE TO RELATED APPLICATION

This application is related to commonly assigned application Ser. No. 478,763, filed June 12, 1974, for PRESSURE SENSOR APPARATUS, by Thomas S. Bustard et al., now abandoned.

BACKGROUND OF THE INVENTION

The need for a non-invasive technique for measuring the pressure in body cavities fo animals or humans is recognized as highly desirable for continuous or intermittent monitoring of body conditions. Such cavities as the cranium, vena cava, bladder, and others provide valuable and sometimes critical information for maintaining the well being or survival of an animal or human. For example, it is known that intercranial pressure provides a valuable indication of well being for a variety of clinical conditions.

A long-term, non-invasive monitor of intracranial pressure is particularly desirable for the congenital hydrocephalic. This condition is one in which the normal production of cerebral spinal fluid is not balanced by reabsorption of the fluid. The retained fluid increases the intracranial pressure and causes head swelling which is a characteristic of hydrocephalus. The increase in intracranial pressure can eventually lead to disability or death.

The normal treatment for hydrocephalus comprises surgically implanting a fluid shunt to transfer cerebrospinal fluid from the intracranial cavity to other parts of the body such as the peritoneal cavity or the jugular vein. The surgically implanted shunt is basically a drainage tube which contains a check valve and requires a modest pressure differential for the cerebrospinal fluid to flow. These shunts often become partially or even fully blocked and intracranial pressure starts to rise resulting in intracranial hypertension.

The symptoms characteristic of a blocked shunt are also characteristic of various other maladies. Early symptoms of a clogged shunt are nausea, headache, and dizziness, any of which can result from many other causes other than intracranial hypertension. In young children especially a physician cannot easily determine shunt blockage without performing a surgical procedure. The presence of an indwelling pressure sensor would permit the physician to directly monitor the intracranial pressure and remove a substantial amount of the risk from his diagnosis.

An additional problem associated with a blocked vent is the rate at which the pressure can rise. Drastic increases can occur within less than an hour. Since a high pressure that is maintained for a period of time will cause irreversible brain damage, it is imperative that pressure increases be discovered in the shortest possible time. Full utilization of a pressure sensor requires a simplified determination of the pressure so that even a parent can perform the determination.

Against this background, there is a recognized and long felt need for a device which overcomes the aforementioned disadvantages and provides a sensor having a self-contained, long-term energy source with compensation for ambient pressure variations and low sensitivity to temperature changes.

The pressure sensor of the present invention is designed to eliminate many of the previously mentioned problems. Once the pressure sensor is installed by a competent surgeon, the pressure can be read non-invasively by a physician with a minimal amount of special equipment. If an attending physician is not readily available, equipment can be installed in the child's home and the parents instructed in its use.

SUMMARY OF THE INVENTION

The pressure sensor of the present invention is fully implantable and contains a radioactive material so that the pressure can be readout non-invasively. In its preferred form, the sensor system comprises a Bourdon or bellows type pressure gauge. Non-radioactive fluid is contained in the pressure gauge which is in communication with a flexible member such as a metallic disc or corrugated bellows tambour placed in the body cavity and exposed to the pressure to be sensed. The pressure gauge is located external to the cavity being sensed and preferably situated just under the skin. The pressure acting upon the flexible member causes radioactive material associated with the pressure gauge to move. The movement of radioactive material is sensed from outside the skin by a conventional nuclear counter or crystal detector instrument.

The application of the present invention to hydrocephalus greatly facilitates treatment of the defect. The pressure sensor of the present invention when used as an intracranial pressure sensor device has a long life, is fully implantable and does not require any energy source other than the radioactive material contained in the device. Two of the major advantages of the present invention are the elimination of implanted energy sources, such as batteries, to operate the device, and the elimination of leads or other penetrations through the skin to provide power or transmit a signal. With a long-lived radioisotope such as promethium 145, the inventive pressure sensing device can be fully implanted and left in place for the life of the patient. Furthermore, the invention contemplates a design and a selection of materials that will assure a negligible radiation dosage to the patient. Although in this application, the invention is primarily intended for a long-term implantation in hydrocephalic children, one may easily appreciate its value in short-term monitoring of head trauma patients.

The inventive pressure monitoring system can be fully implanted with no tubing or wires penetrating the skin, functions accurately to within several millimeters of water pressure and is unaffected by variations in ambient pressure. Also, it is generally insensitive to ambient temperature. Furthermore, the materials used to construct the devices according to the present invention are biologically inert and do not pose any health hazard to the animal or human subject or make the subject more susceptible to mechanical trauma. The sensor unit is of relatively small size and so does not produce unsightly bulging when implanted subdermally.

Other features and advantages of the invention will be apparent from the following description of the preferred embodiments of the invention as shown in the accompanying drawings.

DESCRIPTION OF THE PREFERRED EMBODIMENTS

Figure 1:
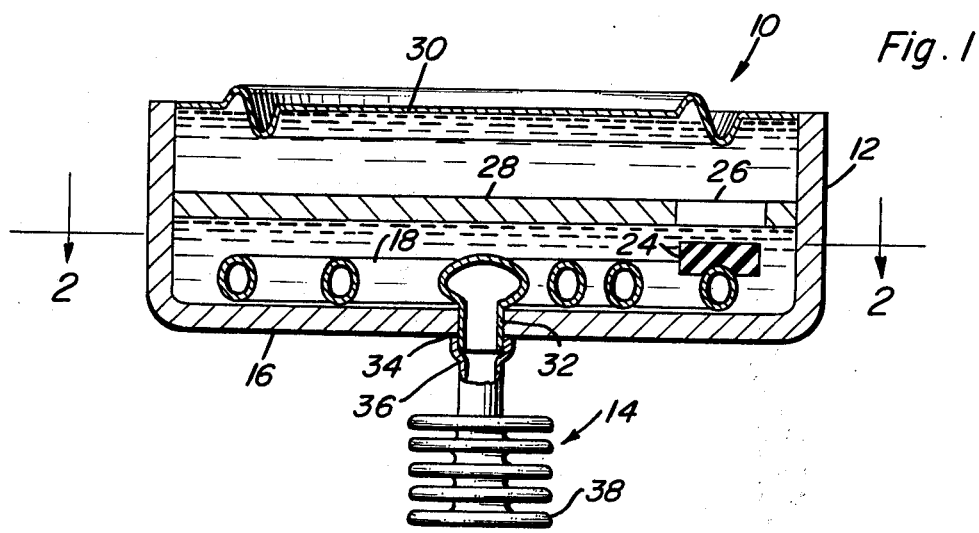
FIG. 1 is a vertical, cross-sectional view of one embodiment of the pressure sensor apparatus of the present invention.

Pressure sensor 10 broadly comprises housing 12 and flexible container or tambour 14. Mounted on base 16 of housing 12 is Bourdon tube 18 which comprises a curved tube of flattened cross-section made of spring bronze or stainless steel. The Bourdon tube may be made in any of a number of shapes and is illustrated in the form of a spiral in FIGS. 1 and 2 and in the form of a C tube in FIG. 4. One end 20 of Bourdon tube 18 is fixed to the pressure inlet and the other end 22 moves proportionally to the pressure difference existing between the inside of Bourdon tube 18. Attached to end 22 of Bourdon tube 18 is radioactive material 24 which is positioned below window 26 in shield plate 28. Top 30 of housing 12 comprises a resilient member or diaphragm. Bourdon tube 18 is fluidly connected to tambour 14 by means of tube 32 which fits into port 34 in base 16 of housing 12 and into opening 36 in the end of tambour 14.

Tambour 14 is filled with a non-radioactive fluid and is placed in the body cavity such as the cranium, bladder, or vena cava of an animal or human for sensing the pressure of the body cavity. Since tambour 14 is normally used in association with the body, the non-radioactive fluid must be inert with respect to the body, or in other words, must be biologically harmless. Furthermore, temperature changes will cause a slight change in the proportion of fluid in tambour 14. Accordingly, it is desirable to use a non-radioactive fluid which has a small volumetric expansion coefficient with temperature. Water is the preferred non-radioactive fluid because of its compatibility with the animal or human body and its small volumetric expansion coefficient of 0.0002 percent degree centigrade. However, any other fluid can be used which meets the above criteria. In particular it is desirable that the fluid have a volumetric change of less than approximately 0.02 percent per degree centigrade which corresponds to a pressure variation of less than 1 millimeter water per degree centigrade.

Figure 2:
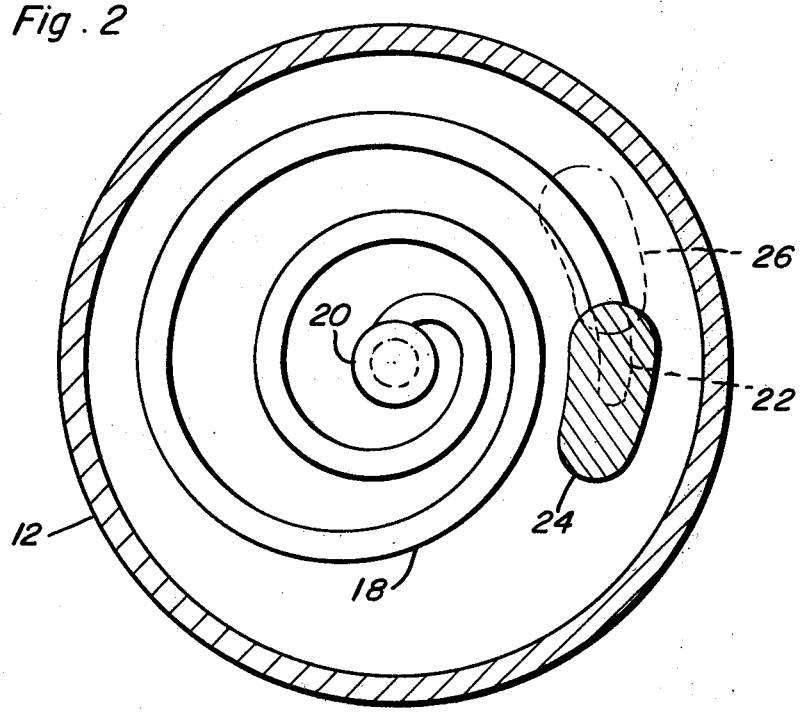
FIG. 2 is a horizontal, cross-sectional view of the embodiment of FIG. 1 taken along line 2—2 of FIG. 1 with the window in the shielding shown schematically.
Figure 3:
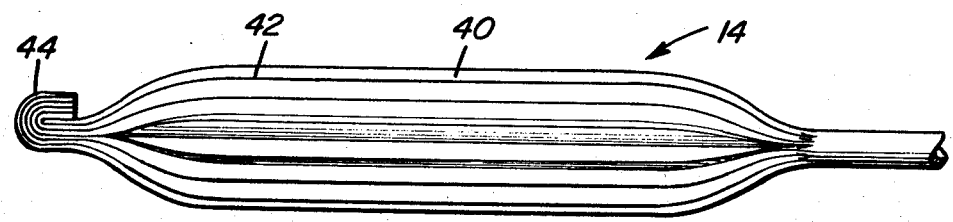
FIG. 3 is a side view of an alternative embodiment of the flexible tambour shown in FIG. 1.

Tambour 14 must be constructed of a flexible material so that it will be responsive to pressure changes and a material which is impermeable to the non-radioactive fluid and in particular to water. A desirable material from the standpoint of flexibility and tissue compatibility is silicone rubber such as the elastomer sold under the trademark Silastic. However, extensive experimentation has shown that silicone rubber tambours cannot be used because of loss of fluid through the wall of the tambour. It was recently discovered that butyl rubber which has a low diffusion coefficient for water is a suitable material from which the tambour can be fabricated. This discovery is disclosed and claimed in the commonly assigned application cross-referenced above. It has now been discovered that metallic tambours fabricated from metals such as tantalum and titanium are suitable for use because of their impermeability. As shown in the embodiment of FIG. 1, the metallic tambour can be fabricated in the shape of a disc bellows or, as shown in FIG. 3, in the shape of a corrugated bellows. The disc bellows tambour is particularly suited to be placed in the intracranial space between the brain and cranium and the corrugated bellows tambour in the lobes between the brain. The disc bellows of FIG. 1 comprises a plurality of disc-shaped sections 38 suitably joined together and the corrugated bellows of FIG. 3 comprises body portion 40, corrugations 42 and crimped and sealed end 44 which is closed after non-radioactive fluid is placed therein. The tambour can be coated with a thin coating of silicone rubber if desired to provide better tissue compatibility. Tambour 14 is essentially a flexible container which can be formed in any suitable shape.

Sensor 10 is constructed so that it is only responsive to pressure changes in the body cavity being sensed and is not responsive to ambient pressure changes. In the embodiment of FIG. 1, housing 12 is filled with a non-radioactive fluid such as used in tambour 14 and diaphragm 30 is directly exposed to the ambient pressure. Accordingly, changes in ambient pressure will be exerted equally on both flexible tambour 14 and diaphragm 30 making sensor 10 responsive only to changes in body cavity pressure sensed by tambour 14.

Housing 12 is preferably constructed of titanium and suitably secured together by bolts, screws or the like. Diaphragm 30 can be constructed of a water impermeable elastomer such as butyl rubber or a thin metallic foil. In the case of butyl rubber, it may be desirable to use a leaf spring in conjunction therewith to prevent cold flow. Tubing 32 is also preferably constructed of titanium. Shield plate 28 preferably comprises tantalum shielding; however, tungsten, iridium, rhenium, platinum, rhodium, gold, niobium, or other suitable heavy metals can be used. All tubing, housing and diaphragm joints are suitably formed by brazing or the use of suitable gaskets, etc. Finally, the entire sensor can be coated with a thin coating of silicone rubber or placed in a silicone rubber boot if desired to provide better tissue compatibility.

Changes in pressure in the body cavity being monitored compress tambour 14 and cause fluid to flow from tambour 14 through tubing 32 and into Bourdon tube 18 in housing 12. Tambour 14 offers effectively no resistance to the pressure change because of its flexible construction. As Bourdon tube 18 tends to straighten under increasing body cavity pressure, it moves radioactive material 24 under window 26. Since the count rate is directly dependent on the quantity of radioactive material exposed through window 26, the body cavity pressure can immediately be determined via the count rate.

Figure 4:
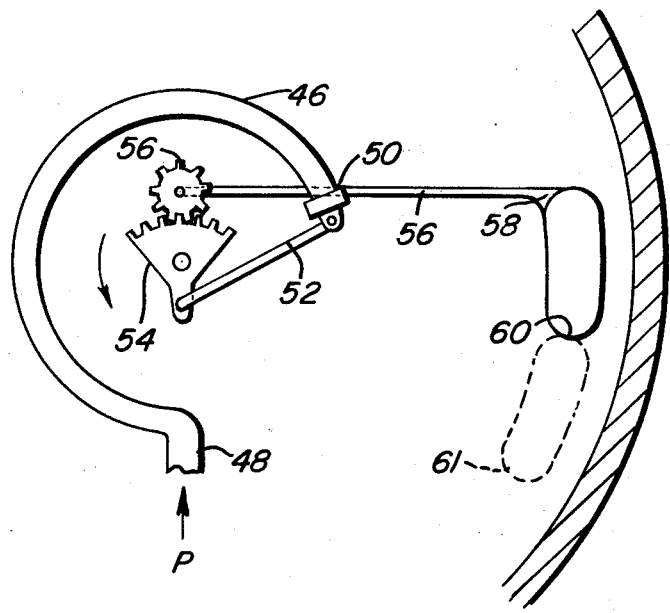
FIG. 4 is a schematic drawing of an alternative embodiment of the Bourdon pressure gauge of FIG. 1 showing mechanical amplification of the pressure sensed.

The movement of radioactive material 24 can be suitably amplified either mechanically or hydraulically. A typical mechanical amplification system is shown in FIG. 4 which shows Bourdon tube 46 which is mounted in a housing in similar manner to Bourdon tube 18 in FIG. 1. One end 48 of Bourdon tube 46 is connected to a tambour depicted by the letter "P" and the other end 50 connected to link 52. The movement of end 50 is transmitted through sector 54 and pinion 56 mechanisms to arm 56 on the end 58 of which is mounted radioactive material 60 positioned below a suitably shaped window 61 in a shield plate such as shown in FIG. 1.

Figure 5:
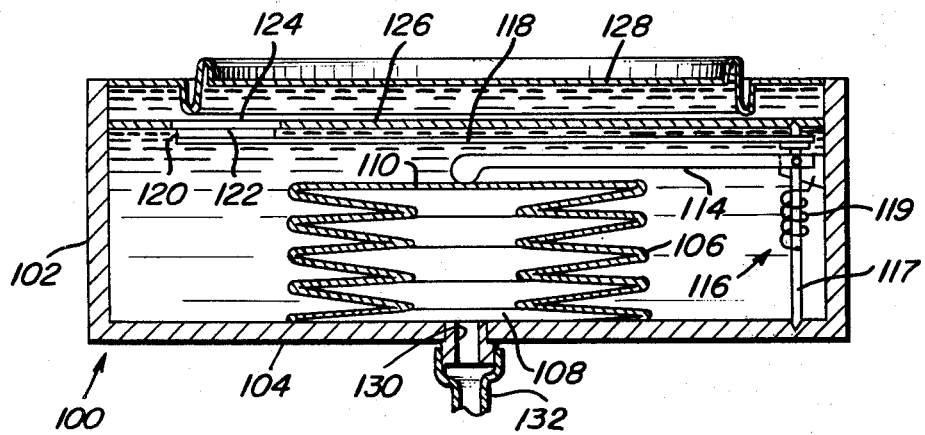
FIG. 5 is a vertical, cross-sectional view of another embodiment of the pressure sensor apparatus of the present invention.

FIG. 5 shows another embodiment of the pressure sensor of the present invention. In this embodiment, the Bourdon tube gauge is replaced by a bellows gauge. More specifically, pressure sensor 100 comprises housing 102 on the base 104 of which is mounted bellows 106. Bellows 106 is preferably formed from a metal such as titanium or tantalum having a suitable spring constant. One end 108 of bellows 106 is fixed to the pressure inlet and the other end 110 moves proportionally to the pressure sensed. Resting against the end 110 of bellows 106 is arm 114 which is connected by linkage 116 to arm 118. Linkage 116 comprises pivot pin 117 which is connected to arm 118 and is cam action rotated by the movement of arm 114. Spring 119 is used to bias arm 114 downward maintaining contact with bellows 110 and biasing arm 118 away from window 124. Attached to end 120 of arm 118 is radioactive material 122 which is positioned below window 124 in shield plate 126. Top 128 of housing 102 comprises a diaphragm to compensate for changes in ambient pressure as in the embodiment of FIG. 1.

Attached to housing 102 by tube 130 tambour 132. Tambour 132 is the same as tambour 14 in FIG. 1. In this embodiment, tambour 132 is placed in contact with the body cavity to be sensed and changes in pressure in the body cavity cause non-radioactive fluid to pass through tube 130 and into bellows 106 causing end 110 thereof to move. This linear movement of end 110 is converted into rotational movement of arm 120 by arm 114 and linkage 116 causing radioactive material 122 to move into window 124.

Figure 6:
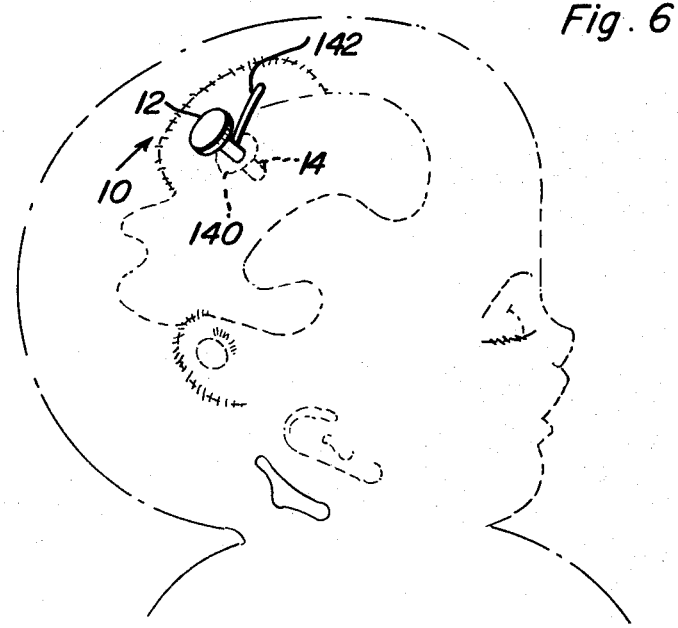
FIG. 6 is a schematic drawing of the pressure sensor of FIG. 1 placed in the head of a child.

FIG. 6 shows pressure sensor 10 of FIG. 1 in use as an intracranial pressure sensor. As seen in FIGS. 6, no external leads are required and the sensor occupies very little space under the scalp so that it produces only a slight elevation thereof. Tambour 14 is placed through burr hole 140 within a cerebral ventrical and housing 12 is positioned outside the skull, but implanted under the scalp. After tambour 14 is inserted through burr hole 140, pressure sensor 10 can be calibrated by pressurizing tambour 14 externally via tube 142 connected by a tee to the neck portion of tambour 14 and using a manometer in combination with a detector. The movement of radioactive material past window 26 in shield plate 28 is detected by measuring the change in radioactivity immediately adjacent to the skin as the tambour 14 is pressurized and correlating this data. Hence, toward the end of the procedure calibration takes place in situ to account for any variations or deformation to the device which may have occurred during the procedure or otherwise. When calibration is completed the tube 142 is crimped or closed off. After the procedure is completed and the incision closed, the skin does not have to be penetrated to obtain reliable pressure information. The quantity of the radioisotope utililzed in the device is extremely small, typically less than one microcurie and results in surface dose rates to the scalp and skull which are on the order of 100 times less than the rates necessary to cause detectable changes in the most radiosensitive body tissue and thus will not adversely affect the adjacent skin or bone marrow.

The radioisotope used in the present invention should have a half life which is sufficiently long to give acceptable end-of-life pressure data. The radioisotope should also be safe as a source of radiation when used immediately beneath the scalp or within a body cavity so that no damage will occur if it is inadvertently released into the body. Another requirement is that the radioisotope must be detected efficiently which means that it must have a high skin transmissibility as well as a high detector efficiency.

The preferred radioisotope used in the present invention is promethium 145. Promethium has an 18 year half life and a soft gamma emission which can be easily transmitted through the skin and efficiently detected while being safely used in quantities necessary for statistical counting accuracy. Among other radiosotopes which can be used in the invention is holmium 163 which has a 40 to 60 year life. The radioisotope is preferably mixed in an epoxy binder so that a solid material can be used.

While the pressure sensor of the present invention has been illustrated primarily as an intracranial pressure sensor, it should be understood that the sensor is also useful in other body cavities in the treatment or care of animals and humans. Thus, valuable information may be derived from monitoring pressure in the vena cava, bladder, or some other body cavity, the foregoing details with respect to intracranial pressure being but a specific illustration of the application of the present invention to a particular problem, and, in that sense, illustrative rather than limiting. Furthermore, while the preferred embodiments of the invention have been disclosed, it should be understood that the invention is not limited to such embodiments. For example, the radioactive material can be in the form of an encapsulated liquid rather than a solid. Accordingly, the present invention should only be limited as defined in the appended claims.

What is claimed is:

1. A pressure sensor for monitoring the pressure in a body cavity comprising, in combination, a housing, a radioactive source disposed within said housing, radiation shielding means associated with said housing, pressure gauge means for positioning said radioactive source and said radiation shielding means in a shielding relationship, pressure responsive means communicating with said housing interior for sensing the pressure in a body cavity, said pressure responsive means being arranged to transmit the pressure in said body cavity to said housing interior to change said shielding relationship between said radioactive source and said radiation shielding means as a function of the pressure in said body cavity and means for amplifying said pressure transmitted from said body cavity to produce an amplified radioactive output proportional to the pressure in said body cavity.

2. A pressure sensor for monitoring the pressure in a body cavity comprising, in combination, a housing having an interior, a radioactive source disposed within said housing interior, radiation shielding means disposed within said housing interior, pressure gauge means in said housing interior for positioning said radioactive source and said radiation shielding means in a shielding relationship, pressure responsive means communicating with said housing interior for sensing the pressure in a body cavity, said pressure responsive means being arranged to transmit the pressure in said body cavity to said pressure gauge means for changing said shielding relationship between said radioactive source and said radiation shielding means as a function of the pressure in said body cavity and means for amplifying said pressure transmitted from said body cavity to produce an amplified radioactive output from said pressure sensor proportional to the pressure in said body cavity.

3. The pressure sensor in accordance with claim 2 wherein said radioactive source comprises a discrete mass of radioactive material operably associated with said pressure gauge means.

4. The pressure sensor in accordance with claim 2 wherein said pressure gauge means comprises a Bourdon tube.

5. The pressure sensor in accordance with claim 2 wherein said pressure gauge means and said amplification means together comprise a Bourdon tube of spiral shape.

6. The pressure sensor in accordance with claim 2 wherein said pressure gauge means and said amplification means together comprise a Bourdon tube of C-shape operably associated with mechanical amplification means.

7. The pressure sensor in accordance with claim 2 wherein said pressure gauge means comprises a bellows.

8. The pressure sensor in accordance with claim 7 wherein said amplification means comprises mechanical output linkage connected to said bellows.

9. The pressure sensor in accordance with claim 2 wherein said pressure responsive means comprises a metallic disc bellows.

10. The pressure sensor in accordance with claim 2 wherein said pressure responsive means comprises a metallic corrugated bellows.

11. The pressure sensor in accordance with claim 2 wherein said radiation shielding has a window therein for monitoring said radioactive source.

12. The pressure sensor in accordance with claim 2 and further comprising means connected to said pressure responsive means to enable calibration after implantation.

13. An intracranial pressure sensor apparatus of the type to be positioned between the scalp and skull and having a pressure transferring mechanism extending through the skull into the intracranial cavity comprising a rigid, transfer housing adapted to be positioned between the skull and scalp, pressure gauge means mounted in said housing to divide said housing into first and second chambers, first pressure sensing means connected at one end to said first chamber and having its other end adapted to be positioned inside the skull, a first non-radioactive fluid contained within said first pressure sensing means and said first chamber, said pressure sensing means being flexible and impermeable to said first non-radioactive fluid, second pressure sensing means connected to said second chamber and adapted to be exposed to pressure between the scalp and skull, a second non-radioactive fluid contained within said second pressure sensing means and said second chamber, said second pressure sensing means being flexible and impermeable to said second non-radioactive fluid, radioactive material contained within said transfer housing and radiation shielding means at least partially surrounding said radioactive material, said radioactive material being operatively connected to said pressure gauge means whereby pressure acting upon said first pressure sensing means within the skull will cause said pressure gauge means to move and said radiation shielding means to shield said radioactive material as a function of said pressure, said radioactive material adapted to being sensed externally of the scalp by a radiation detector, said second pressure sensing means acting to compensate for changes in ambient pressure externally of the scalp.

14. A pressure sensor comprising a housing, bellows means defining a chamber in said housing, flexible means in communication with said chamber, a non-radioactive liquid contained within said chamber and said flexible means so that pressure acting upon said flexible means will cause said bellows means to contract and expand, radiation shielding means associated with said housing, amplification means and a radioactive material connected to said bellows means by said amplification means and being at least partially surrounded by said radiation shielding means, said radiation shielding means shielding said radioactive material as a function of the pressure acting upon said flexible means.

15. The pressure sensor in accordance with claim 14 and further comprising ambient pressure responsive means communicating with said housing interior for transmitting ambient pressure to said bellows means to compensate for changes in ambient pressure.

* * * * *

UNITED STATES PATENT OFFICE
CERTIFICATE OF CORRECTION

PATENT NO. : 3,977,391
DATED : August 31, 1976
INVENTOR(S) : Lewis Fleischmann

It is certified that error appears in the above-identified patent and that said Letters Patent are hereby corrected as shown below:

Column 1, line 12, change "fo" to --of--.

Column 6, line 16, after "year" insert --half--.

Signed and Sealed this

Fourteenth Day of December 1976

[SEAL]

Attest:

RUTH C. MASON
Attesting Officer

C. MARSHALL DANN
Commissioner of Patents and Trademarks